(12) United States Patent
Timken (10) Patent No.: US 11,174,437 B2
(45) Date of Patent: Nov. 16, 2021

(54) CIRCULAR ECONOMY FOR PLASTIC WASTE TO POLYPROPYLENE VIA REFINERY FCC AND ALKYLATION UNITS

(71) Applicant: Chevron U.S.A. Inc., San Ramon, CA (US)

(72) Inventor: Hye-Kyung Timken, Albany, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 0 days.

(21) Appl. No.: 17/131,877

(22) Filed: Dec. 23, 2020

(65) Prior Publication Data
US 2021/0189249 A1 Jun. 24, 2021

Related U.S. Application Data

(60) Provisional application No. 62/952,845, filed on Dec. 23, 2019.

(51) Int. Cl.
*C10B 53/07* (2006.01)
*C10G 31/06* (2006.01)
(Continued)

(52) U.S. Cl.
CPC ............. *C10B 53/07* (2013.01); *C10G 31/06* (2013.01); *C10G 35/02* (2013.01); *C10G 51/023* (2013.01);
(Continued)

(58) Field of Classification Search
None
See application file for complete search history.

(56) References Cited

U.S. PATENT DOCUMENTS 3,845,157 A   10/1974   Woo et al.
4,642,401 A   2/1987   Coenen et al.
(Continued)

FOREIGN PATENT DOCUMENTS

EP   0620264 A2   10/1994

OTHER PUBLICATIONS

"Refineries: Application Focus—HF Alkylation", Pall Corporation, 2018, pp. 1-2; https://www.pall.co.uk/content/dam/pall/oil-gas/literature-library/non-gated/pdf/refinery-hf-alkylation.pdf.
(Continued)

*Primary Examiner* — Tam M Nguyen
(74) *Attorney, Agent, or Firm* — E. Joseph Gess; Melissa M. Hayworth; Terrence M. Flaherty (57) ABSTRACT

Provided is a continuous process for converting waste plastic into recycle for polypropylene polymerization. The process comprises selecting waste plastics containing polyethylene and/or polypropylene and passing the waste plastics through a pyrolysis reactor to thermally crack at least a portion of the polyolefin waste and produce a pyrolyzed effluent. The pyrolyzed effluent is separated into offgas, a naphtha/diesel fraction, a heavy fraction, and char. Pyrolysis oil and wax, comprising the naphtha/diesel fraction and heavy fraction, is sent to a refinery FCC unit. A liquid petroleum gas $C_3$-$C_5$ olefin/paraffin mixture is recovered from the FCC unit and passed to a refinery alkylation unit. A propane fraction is recovered from the alkylation unit and passed to a dehydrogenation unit to produce propylene. The propylene is passed to a propylene polymerization reactor.

13 Claims, 3 Drawing Sheets

Establishment of Circular Economy for Recycle of PP via Pyrolysis of PE/PP Waste Plastics Through Oil Refinery Operation (51) Int. Cl.
*C10G 35/02* (2006.01)
*C10G 51/02* (2006.01)
*C10G 57/02* (2006.01)

(52) U.S. Cl.
CPC ..... *C10G 57/02* (2013.01); *C10G 2300/1003* (2013.01); *C10G 2300/1044* (2013.01); *C10G 2400/04* (2013.01); *C10G 2400/06* (2013.01); *C10G 2400/08* (2013.01); *C10G 2400/20* (2013.01); *C10G 2400/22* (2013.01); *C10G 2400/28* (2013.01)

(56) References Cited

U.S. PATENT DOCUMENTS

| | | |
|---|---|---|
| 5,849,964 A | 12/1998 | Holighaus et al. |
| 6,143,940 A | 11/2000 | Miller et al. |
| 6,150,577 A | 11/2000 | Miller et al. |
| 6,288,296 B1 | 9/2001 | Miller et al. |
| 6,774,272 B2 | 8/2004 | Miller |
| 6,822,126 B2 | 11/2004 | Miller |
| 7,834,226 B2 | 11/2010 | Miller |
| 8,088,961 B2 | 1/2012 | Miller |
| 8,404,912 B1 | 3/2013 | Miller |
| 8,480,880 B2 | 7/2013 | Miller |
| 8,696,994 B2 | 4/2014 | Miller |
| 2009/0250376 A1* | 10/2009 | Brandvoid ............... C10G 3/49 208/17 |
| 2009/0253948 A1* | 10/2009 | McCall .................... C10G 3/50 585/240 |
| 2009/0301930 A1* | 12/2009 | Brandvoid ............... C10L 1/04 208/17 |
| 2013/0317270 A1 | 11/2013 | Vanderbilt et al. |
| 2016/0264885 A1 | 9/2016 | Narayanaswamy et al. |
| 2016/0362609 A1* | 12/2016 | Ward ....................... C10G 1/10 |
| 2019/0161683 A1 | 5/2019 | Narayanaswamy et al. |
| 2019/0284476 A1* | 9/2019 | Gaber .................... C10G 1/002 |
| 2019/0367428 A1 | 12/2019 | Ramamurthy et al. |
| 2021/0189248 A1 | 6/2021 | Timken |
| 2021/0189250 A1 | 6/2021 | Timken |
| 2021/0189251 A1 | 6/2021 | Timken |
| 2021/0189252 A1 | 6/2021 | Timken |
| 2021/0189253 A1 | 6/2021 | Timken |
| 2021/0189254 A1* | 6/2021 | Timken ..................... C07C 4/06 |

OTHER PUBLICATIONS

International Search Report and Written Opinion dated Mar. 15, 2021 in PCT/US2020/066806.

* cited by examiner

Figure 1 (base case)
Pyrolysis of Waste Plastics to Fuel or Wax

Figure 2

Establishment of Circular Economy for Recycle of PP via Pyrolysis of PE/PP Waste Plastics Through Oil Refinery Operation Figure 3
Plastic Type Classification for Waste Plastics Recycling

CIRCULAR ECONOMY FOR PLASTIC WASTE TO POLYPROPYLENE VIA REFINERY FCC AND ALKYLATION UNITS

CROSS REFERENCE TO RELATED APPLICATIONS

The present application claims priority to U.S. Provisional Application No. 62/952,845 filed Dec. 23, 2019, the complete disclosure of which is incorporated herein by reference in its entirety.

BACKGROUND

The world has seen extremely rapid growth of plastics production. According to PlasticsEurope Market Research Group, the world plastics production was 335 million tons in 2016, 348 million tons in 2017 and 359 million tons in 2018. According to McKinsey & Company, the global plastics-waste volume was estimated about 260 million tons per year in 2016, and projected to be 460 million tons per year by 2030 if the current trajectory continues.

Single use plastic waste has become an increasingly important environmental issue. At the moment, there appear to be few options for recycling polyethylene and polypropylene waste plastics to value-added chemical and fuel products. Currently, only a small amount of polyethylene and polypropylene is recycled via chemical recycling, where recycled and cleaned polymer pellets are pyrolyzed in a pyrolysis unit to make fuels (naphtha, diesel), stream cracker feed or slack wax.

Processes are known which convert waste plastic into hydrocarbon lubricants. For example, U.S. Pat. No. 3,845,157 discloses cracking of waste or virgin polyolefins to form gaseous products such as ethylene/olefin copolymers which are further processed to produce synthetic hydrocarbon lubricants. U.S. Pat. No. 4,642,401 discloses the production of liquid hydrocarbons by heating pulverized polyolefin waste at temperatures of 150-500° C. and pressures of 20-300 bars. U.S. Pat. No. 5,849,964 discloses a process in which waste plastic materials are depolymerized into a volatile phase and a liquid phase. The volatile phase is separated into a gaseous phase and a condensate. The liquid phase, the condensate and the gaseous phase are refined into liquid fuel components using standard refining techniques. U.S. Pat. No. 6,143,940 discloses a procedure for converting waste plastics into heavy wax compositions. U.S. Pat. No. 6,150,577 discloses a process of converting waste plastics into lubricating oils. EP0620264 discloses a process for producing lubricating oils from waste or virgin polyolefins by thermally cracking the waste in a fluidized bed to form a waxy product, optionally using a hydrotreatment, then catalytically isomerizing and fractionating to recover a lubricating oil.

Other documents which relate to processes for converting waste plastic into lubricating oils include U.S. Pat. Nos. 6,288,296; 6,774,272; 6,822,126; 7,834,226; 8,088,961; 8,404,912 and 8,696,994; and U.S. Patent Publication Nos. 2019/0161683; 2016/0362609; and 2016/0264885. The foregoing patent documents are incorporated herein by reference in their entirety.

The current method of chemical recycling via pyrolysis cannot make a big impact for the plastics industry. The current pyrolysis operation produces poor quality fuel components (naphtha and diesel range products), but the quantity is small enough that these products can be blended into fuel supplies. However, this simple blending cannot continue if very large volumes of waste polyethylene and polypropylene are to be recycled to address environmental issues. The products as produced from a pyrolysis unit are of too poor quality to be blended in large amounts (for example 5-20 vol. % blending) in transportation fuels.

Yet, in order to achieve recycling of single use plastics in an industrially significant quantity to reduce its environmental impact, more robust processes are needed. The improved processes should establish "circular economy" for the waste polyethylene and polypropylene plastics where the spent waste plastics are recycled effectively back as starting materials for polymers and high value byproducts.

SUMMARY

Provided is a continuous process for converting waste plastic into recycle for polypropylene polymerization. The process comprises selecting waste plastics containing polyethylene and/or polypropylene, and passing the waste plastics through a pyrolysis reactor to thermally crack at least a portion of the polyolefin waste and produce a pyrolyzed effluent. The pyrolyzed effluent is separated into offgas, a naphtha/diesel fraction, a heavy fraction, and char.

The incorporation of the process with an oil refinery is an important aspect of the present process, and allows the creation of a circular economy with a single use waste plastics such as polypropylene. Thus, the pyrolysis oil and optionally pyrolysis wax, which comprises the naphtha/diesel fraction and heavy fraction, is passed to a refinery FCC unit from which a liquid petroleum gas $C_3$-$C_5$ olefin/paraffin mixture is recovered. The liquid petroleum gas fraction is passed to a refinery alkylation unit. A propane fraction is recovered from the alkylation unit and passed to a dehydrogenation unit to produce propylene.

The refinery will generally have its own hydrocarbon feed flowing through the refinery units. The flow volume of pyrolysis oil and wax generated from the pyrolysis of waste plastic to the refinery units can comprise any practical or accommodating volume % of the total flow to the refinery units. Generally, the flow of the pyrolysis oil and wax generated from the waste plastic pyrolysis, for practical reasons, can be up to about 50 vol. % of the total flow, i.e., the refinery flow and the pyrolysis flow. In one embodiment, the flow of the pyrolysis oil and wax is an amount up to about 20 vol. % of the total flow.

Among other factors, it has been found that by adding refinery operations one can upgrade the waste pyrolysis oil and wax to higher value products such as gasoline and diesel. But also, by adding refinery operations it has been found that clean propane and propylene can be efficiently and effectively produced from the waste pyrolysis and for ultimate polypropylene polymer production. Positive economics are realized for the overall process from recycled plastics to a polypropylene product with product quality identical to that of virgin polymer.

DETAILED DESCRIPTION

In the present process, provided is a method to recycle waste polyethylene and/or polypropylene back to virgin polypropylene to establish a circular economy by combining distinct industrial processes. A substantial portion of polyethylene and polypropylene polymers are used in single use plastics and get discarded after its use. The single use plastic waste has become an increasingly important environmental issue. At the moment, there appear to be few options for recycling polyethylene and polypropylene waste plastics to value-added chemicals and fuel products. Currently, only a small amount of polyethylene/polypropylene is recycled via chemical recycling, where recycled and cleaned polymer pellets are pyrolyzed in a pyrolysis unit to make fuels (naphtha, diesel), steam cracker feed or slack wax.

Polypropylene is used widely in various consumer and industrial products. Polypropylene is the second-most widely produced commodity plastic after polyethylene with its mechanical ruggedness and high chemical resistance. Polypropylene is widely used in packaging, film, fibers for carpets and clothing, molded articles and extruded pipes. Today, only a small portion of spent polypropylene products is collected for recycling, due to the inefficiencies and ineffectiveness of the recycling efforts discussed above.

Figure 1:
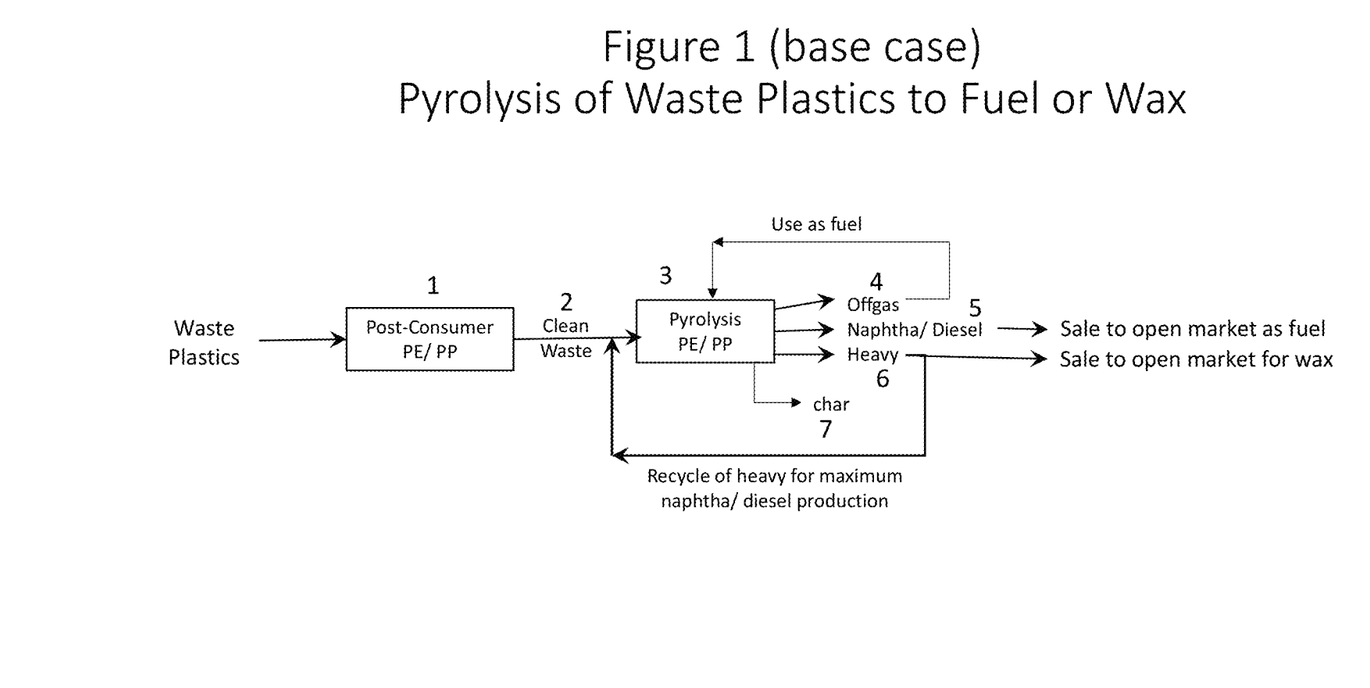
FIG. 1 depicts the current practice of pyrolyzing waste plastics to produce fuel or wax (base case).

FIG. 1 shows a diagram of pyrolysis of waste plastics fuel or wax that is generally operated in the industry today. As noted above, generally, polyethylene and polypropylene wastes are sorted together 1. The cleaned polyethylene/polypropylene waste 2 is converted in a pyrolysis unit 3 to offgas 4 and pyrolysis oil (liquid product). The offgas 4 from the pyrolysis unit is used as fuel to operate the pyrolysis unit 3. An on-site distillation unit separates the pyrolysis oil to produce naphtha and diesel 5 products which are sold to fuel markets. The heavy pyrolysis oil fraction 6 is recycled back to the pyrolysis unit 3 to maximize the fuel yield. Char 7 is removed from the pyrolysis unit 3. The heavy fraction 6 is rich in long chain, linear hydrocarbons, and is very waxy (i.e., forms paraffinic wax upon cooling to ambient temperature). Wax can be separated from the heavy fraction 6 and sold to the wax markets.

The present process converts pyrolyzed polypropylene and/or polyethylene waste plastic in large quantities by integrating the waste polymer pyrolysis product streams into an oil refinery operation. The resulting processes produce the feedstocks for the polymers (liquid petroleum gas (LPG) propane stream for a propane dehydrogenation unit), high quality gasoline and diesel fuel, and/or quality base oil.

Generally, the present process provides a circular economy for polypropylene plants. Polypropylene is produced via polymerization of pure propylene. Clean propylene can be made from a propane dehydrogenation unit. The pure propane for the dehydrogenation unit can be obtained from an oil refinery alkylation unit, which produces a pure propane liquefied petroleum gas (LPG) after alkylation of mixed $C_3$-$C_5$ olefins (from fluid catalytic cracking (FCC)) with isobutane.

By adding refinery operations to upgrade the waste pyrolysis oil and wax to higher value products (gasoline and diesel) and to produce clean propane and propylene for ultimate polypropylene polymer production, positive economics are created for the overall processes from recycled plastics to a polypropylene product with product quality identical to that of the virgin polymer.

A pyrolysis unit produces poor quality products containing contaminants, such as calcium, magnesium, chlorides, nitrogen, sulfur, dienes, and heavy components, which products cannot be used in large quantity for blending in transportation fuels. It has been discovered that by having these products go through the refinery units, the contaminants can be captured in pre-treating units and their negative impacts diminished. The fuel components are further upgraded with appropriate refinery units with chemical conversion processes and the final transportation fuels produced by the integrated process is of higher quality and will meet the fuels quality requirements. The integrated process will generate a much cleaner and pure propane stream for the propane dehydrogenation unit and ultimately for polypropylene production. These large on-spec productions allow "cyclical economy" for the recycle plastics to be feasible.

The carbon in and out of the refinery operations are "transparent," meaning that all the molecules from the waste plastic do not necessarily end up in the exact olefin product cycled back to the polyolefin plants, but are nevertheless assumed as "credit" as the net "green" carbon in and out of the refinery is positive. With these integrated processes, the amount of virgin feeds needed for polypropylene plants will be reduced significantly.

Figure 2:
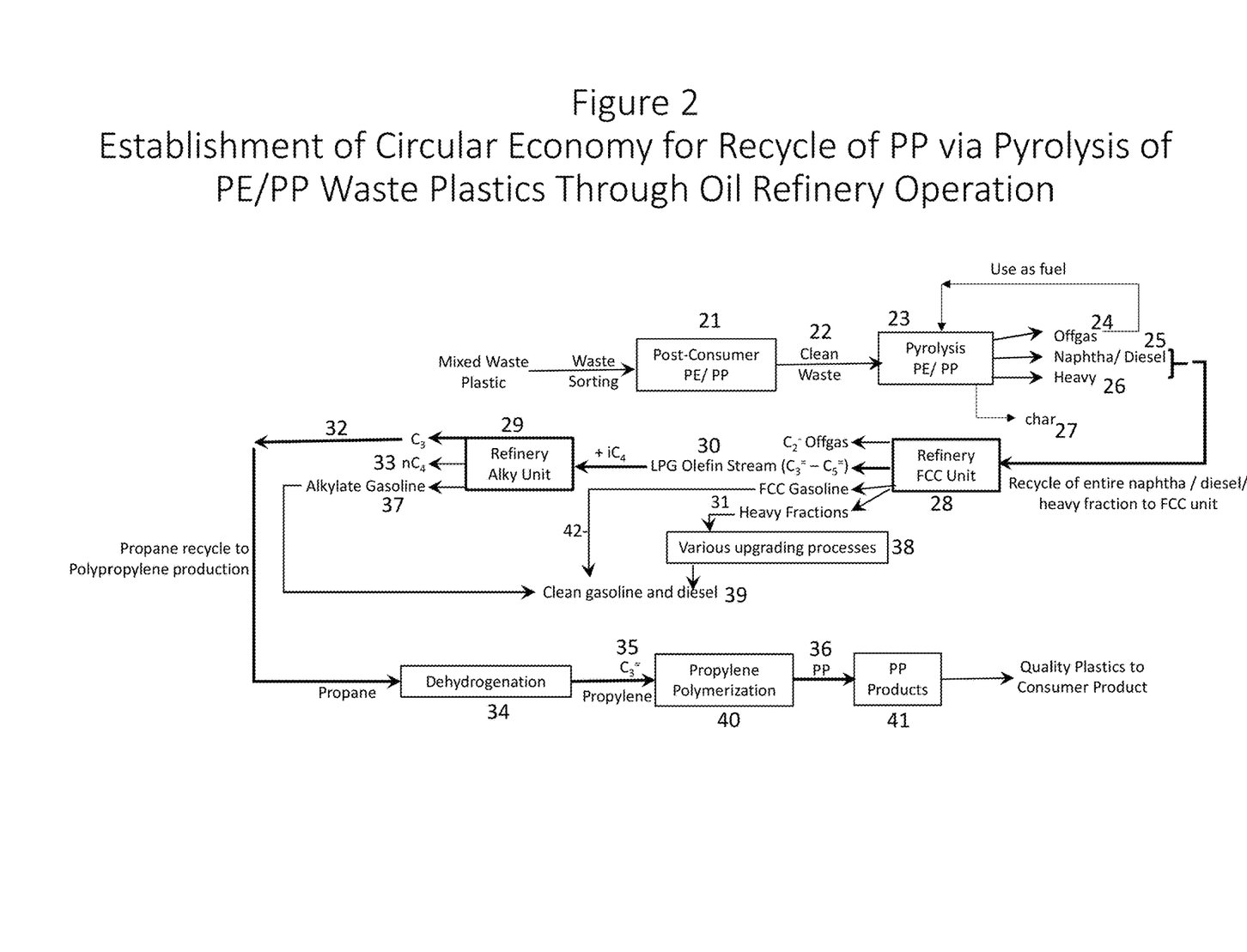
FIG. 2 depicts a present process for establishing a circular economy for waste plastics.
Figure 3:
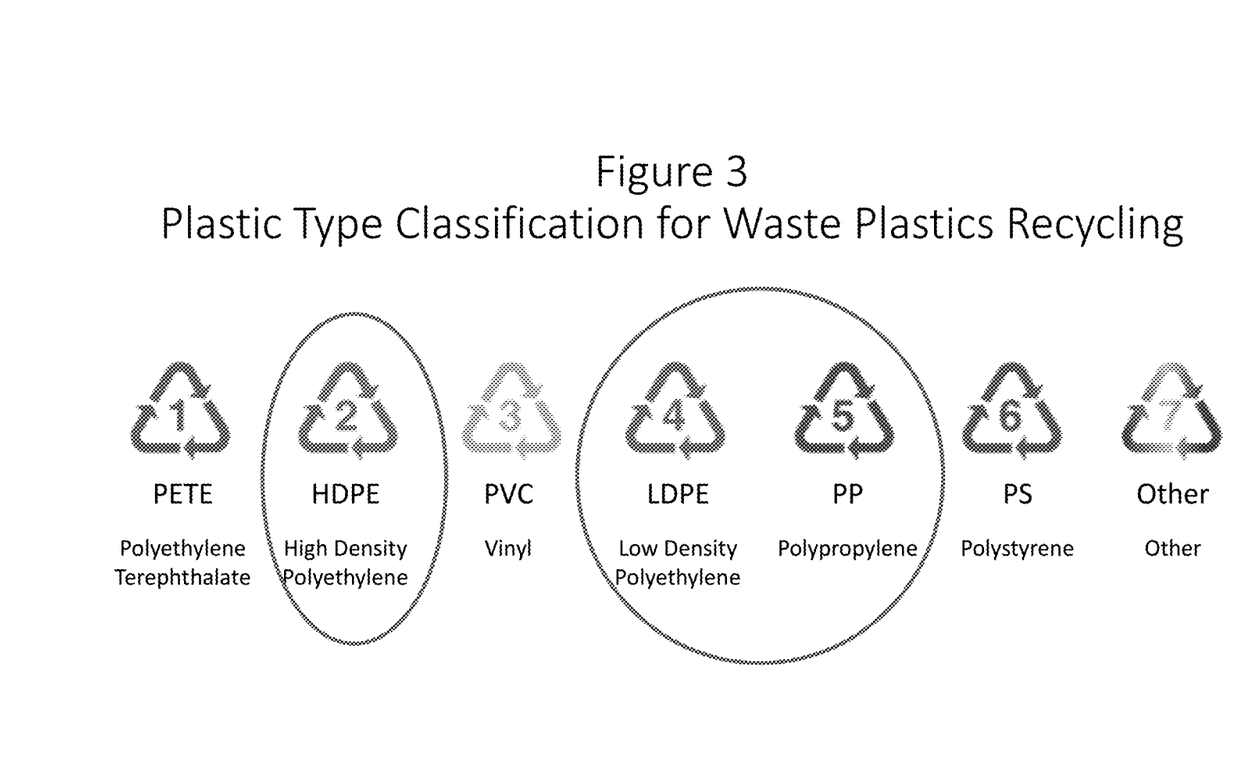
FIG. 3 depicts the plastic type classification for waste plastics recycling.

FIG. 2 shows the present integrated process, integrating refinery operations with recycle for effective polypropylene production. In FIG. 2, mixed waste plastics are sorted together 21. The cleaned waste plastic 22 is converted in a pyrolysis unit 23 to offgas 24 and a pyrolysis oil (liquid product) and optionally wax (solid product at ambient temperature). The offgas 24 from the pyrolysis unit can be used as fuel to operate the pyrolysis unit 23. The pyrolysis oil is separated, generally by an on-site distillation unit, into a naphtha/diesel fraction 25, and a heavy faction 26. Char 27 is removed from the pyrolysis unit 23 after completion of the pyrolysis step.

The pyrolysis unit can be located near the waste plastics collection site, which site could be away from a refinery, near a refinery, or within a refinery. If the pyrolysis unit is located away from the refinery, then pyrolysis oil (naphtha/diesel and heavies) can be transferred to the refinery by truck, barge, rail car or pipeline. It is preferred, however, that the pyrolysis unit is within the plastics collection site or within the refinery.

The preferred starting material for the present process is sorted waste plastics containing predominantly polyethylene and polypropylene (plastics recycle classification types 2, 4, and 5). The pre-sorted waste plastics are washed and shredded or pelleted to feed to a pyrolysis unit for thermal cracking. FIG. 1 depicts the plastic type classification for waste plastics recycling. Classification types 2, 4, and 5 are high density polyethylene, low density polyethylene and polypropylene, respectively.

Proper sorting of waste plastics is very important in order to minimize contaminants such as N, Cl, and S. Plastics waste containing polyethylene terephthalate (plastics recycle classification type 1), polyvinyl chloride (plastics recycle classification type 3) and other polymers (plastics recycle classification type 7) need to be sorted out to less than 5%, preferably less than 1% and most preferably less than 0.1%. The present process can tolerate moderate amount of polystyrene (plastics recycle classification type 6). Waste polystyrene needs to be sorted out to less than 30%, preferably less than 20% and most preferably less than 5%.

Washing of waste plastics removes metal contaminants such as sodium, calcium, magnesium, aluminum, and non-metal contaminants coming from other waste sources. Non-metal contaminants include contaminants coming from the Periodic Table Group IV, such as silica, contaminants from Group V, such as phosphorus and nitrogen compounds, contaminants from Group VI, such as sulfur compounds, and halide contaminants from Group VII, such as fluoride, chloride, and iodide. The residual metals, non-metal contaminants, and halides need to be removed to less than 50 ppm, preferentially less than 30 ppm and most preferentially to less than 5 ppm.

If the washing does not remove the metals, non-metal contaminants, and halide impurities adequately, then a separate guard bed can be used to remove the metals and non-metal contaminants.

The pyrolyzing is carried out by contacting a plastic material feedstock in a pyrolysis zone at pyrolysis conditions, where at least a portion of the feed(s) is cracked, thus forming a pyrolysis zone effluent comprising 1-olefins and n-paraffins. Pyrolysis conditions include a temperature of from about 400° C. to about 700° C., preferably from about 450° C. to about 650° C. Conventional pyrolysis technology teaches operating conditions of above-atmospheric pressures. See e.g., U.S. Pat. No. 4,642,401. Additionally, it has been discovered that by adjusting the pressure downward, the yield of a desired product can be controlled. See, e.g., U.S. Pat. No. 6,150,577. Accordingly, in some embodiments where such control is desired, the pyrolysis pressure is sub-atmospheric.

FIG. 2 shows the present integrated process where the entire liquid fraction from the pyrolysis unit 23 is sent to an FCC unit 28 and then to an alkylation unit 29. The liquid fraction from the pyrolysis unit 23 comprises the naphtha/diesel 25 and heavy 26 fractions. Cracking of the pyrolysis liquid oil combined with petroleum derived oil in the FCC unit produces liquefied petroleum gas (LPG) $C_3$-$C_4$ or $C_3$-$C_5$ olefin/paraffin mixture 30, and a gasoline 42 and heavy fraction 31. The $C_3$-$C_4$ olefin/paraffin mixture 30 from the FCC plant 28 is sent to the alkylation plant 29 which produces pure propane 32 and n-butane 33 streams. The pure propane 32 can be fed to a propane dehydrogenation unit 34 to prepare propylene 35, and ultimately polypropylene 36.

The fluid catalytic cracking (FCC) process is widely used in the refining industry for conversion of atmospheric gas oil, vacuum gas oil, atmospheric residues and heavy stocks recovered from other refinery operations into high-octane gasoline, light fuel oil, heavy fuel oil, olefin-rich light gas (LPG) and coke. FCC uses a high activity zeolite catalyst to crack the heavy hydrocarbon molecules at a 950-990° F. reactor temperature in a riser with a short contact time of a few minutes or less. LPG streams containing olefins (propylene, butylene) are commonly upgraded to make alkylate gasoline, or to be used in chemicals manufacturing. A conventional FCC unit can be used.

The refinery will generally have its own hydrocarbon feed flowing through the refinery units. The flow volume of pyrolysis oil and wax generated from the pyrolysis of waste plastic to the refinery units, here an FCC unit, can comprise any practical or accommodating volume % of the total flow to the refinery units. Generally, the flow of the pyrolysis oil and wax fraction generated from the waste plastic pyrolysis, for practical reasons, can be up to about 50 vol. % of the total flow, i.e., the refinery flow and the pyrolysis flow. In one embodiment, the flow of the pyrolysis oil and wax is an amount up to about 20 vol. % of the total flow. In another embodiment, the flow of the pyrolysis oil and wax is an amount up to about 10 vol. % of the total flow. About 20 vol. % has been found to be an amount that is quite practical in its impact on the refinery while also providing excellent results and being an amount that can be accommodated. The amount of pyrolysis oil generated from the pyrolysis can of course be controlled so that the fraction passed to the refinery units provides the desired volume % of the flow.

Cracking of the pyrolysis liquid oil combined with petroleum derived oil in the FCC unit produces liquefied petroleum gas (LPG) of a $C_3$-$C_5$ olefin/paraffin mixture 30, as well as a gasoline and heavy fraction 31. The $C_3$-$C_5$ olefin/paraffin mixture 30 from the FCC plant is sent to an alkylation plant 29 which produces pure propane 32 and n-butane 33 streams.

An alkylation process combines light olefins (propylene, butylene, typically from FCC unit) with isobutane to produce highly branched paraffinic fuel, alkylate gasoline. Alkylate gasoline is a clean-burning, high-octane, low-sulfur, low-RVP gasoline blending component that does not contain olefinic or aromatic compounds, thus is a very desirable gasoline blending component. Conventional alkylation processes use either sulfuric acid catalyst which operates at 30-60° F. reactor temperature or hydrofluoric acid catalyst that operates at 90-95° F. reactor temperature.

Dehydrogenation of propane is practiced widely in the industry to produce propylene. The reaction is endothermic, conversion is maintained by multi-stage reactors and inter-stage heaters. The unit typically operates at high temperature (>900° F.) and low pressure (<50 psig) in the presence of noble metal (Pt) catalyst. The multi-stage process generates approximately 85% purity propylene/propane mixture. This stream is directed to a propane/propylene (PP) splitter which is a high efficiency distillation column. The splitter produces pure propylene stream with 99.5-99.8% purity.

The propane dehydrogenation unit can be located away from a refinery, near a refinery, or within a refinery. The propane stream is sent from an alkylation unit to a propane dehydrogenation unit by truck, barge, rail car or pipeline. It is preferred that the propane dehydrogenation unit is in close proximity to a refinery alkylation unit or a polypropylene chemical plant.

The propylene prepared in the present process can be polymerized in a propylene polymerization unit 40 to prepare polypropylene, from which polypropylene products 41 can be made.

Polypropylene is produced via chain-growth polymerization from the monomer propylene. A Ziegler-Natta catalyst or metallocene catalyst is used to catalyze the polymerization of propylene to polypropylene polymer with desired properties. These catalysts are activated with special cocatalyst containing an organoaluminum compounds. The industrial polymerization processes uses either gas phase polymerization in a fluidized bed reactor or bulk polymerization in loop reactors. The gas phase polymerization typically runs at 50-90° C. temperature and a pressure of 8-35 atm pressure in the presence of $H_2$. The bulk polymerization proceeds at 60 to 80° C. and 30-40 atm pressure is applied to keep the propylene in liquid state.

The propylene polymerization unit is preferably located near the refinery so that the feedstocks (propane and propylene) can be transferred via pipeline. For a petrochemical plant located away from the refinery, the feedstock can be delivered via truck, barge, rail car or pipeline.

The alkylation unit 29 also produces clean, high octane gasoline 37. Alkylate gasoline 37 and FCC gasoline 42 fractions are sent to a refinery gasoline blending pool 39. The heavy hydrocarbon product 31 from the FCC unit and n-butane stream from the alkylation unit can be sent to appropriate refinery units 38 for upgrading into clean gasoline, diesel, or jet fuel.

The benefits of a circular economy and an effective and efficient recycling campaign are realized by the present integrated process.

The following examples are provided to further illustrate the present process and its benefits. The examples are meant to be illustrative and not limiting.

Example 1: Properties of Pyrolysis Oil and Wax from Commercial Sources

Pyrolysis oil and wax samples were obtained from commercial sources and their properties are summarized in Table 1. These pyrolysis samples were prepared from waste plastics containing mostly polyethylene and polypropylene via thermal decomposition in a pyrolysis reactor at around 400-600° C., near atmospheric pressure without any added gas or a catalyst. A pyrolysis unit typically produces gas, liquid oil product, optionally wax product, and char. The pyrolysis unit's overhead gas stream containing thermally cracked hydrocarbon was cooled to collect condensate as pyrolysis oil (liquid at ambient temperature) and/or pyrolysis wax (solid at ambient temperature). The pyrolysis oil is the main product of the pyrolysis units. Some units produce pyrolysis wax as a separate product in addition to the pyrolysis oil.

using the magnet scanned from 40 to 500 Daltons. Total sulfur was determined using XRF per ASTM D2622 method. The nitrogen was determined using a modified ASTM D5762 method using chemiluminescence detection. The total chloride content was measured using combustion ion chromatography instrument using modified ASTM 7359 method. The oxygen content in naphtha and distillate boiling range was estimated using GC by GC/MS measurements with electron ionization detector for m/Z range of 29-500. Trace metal and non-metal elements in oil were determined using inductively coupled plasma-atomic emission spectrometry (ICP-AES).

Industrial pyrolysis process of sorted plastics, sourced predominantly from polyethylene and polypropylene waste, produced quality hydrocarbon streams with specific gravity ranging 0.7 to 0.9, and a boiling range from 18 to 1100° F. as in pyrolysis oil or pyrolysis wax.

TABLE 1

Properties of As-Received Oil and Wax from Pyrolysis of Waste Plastics

|  | Pyrolysis Oil Sample A | Pyrolysis Oil Sample B | Pyrolysis Oil Sample C | Pyrolysis Oil Sample D | Pyrolysis Wax Sample E |
|---|---|---|---|---|---|
| Specific Gravity at 60° F. | 0.814 | 0.820 | 0.774 | — | 0.828 |
| Simulated Distillation, ° F. | | | | | |
| 0.5% (Initial Boiling Point) | 87 | 299 | 18 | 86 | 325 |
| 5% | 179 | 306 | 129 | 154 | 475 |
| 10% | 214 | 309 | 156 | 210 | 545 |
| 30% | 322 | 346 | 285 | 304 | 656 |
| 50% | 421 | 447 | 392 | 421 | 733 |
| 70% | 545 | 585 | 517 | 532 | 798 |
| 90% | 696 | 798 | 663 | 676 | 894 |
| 95% | 772 | 883 | 735 | 743 | 939 |
| 99.5% (Final Boiling Point) | 942 | 1079 | 951 | 888 | 1064 |
| Carlo-Erba Hydrocarbon Analysis | | | | | |
| Carbon, wt % | 87.6 | 84.21 | 85.46 | 85.97 | 85.94 |
| Hydrogen, wt % | 12.7 | 12.25 | 14.1 | 14.0 | 14.15 |
| Sum of C + H, wt % | 100.3 | 96.46 | 99.5 | 100.0 | 100.1 |
| H/C Molar Ratio | 1.73 | 1.75 | 1.98 | 1.96 | 1.98 |
| Bromine Number, g/100 g | 49 | 60 | 40 | 44 | 14 |
| Hydrocarbon Type | | | | | |
| Total Aromatics, vol % | 23.3 | 22.8 | 5.1 | 8.7 | 13.3 |
| Total Olefins & Naphthenes, vol % | 39.0 | 50.2 | 42.4 | 38.2 | 42.1 |
| Total Paraffins, vol % | 37.7 | 27 | 52.5 | 53.1 | 44.6 |
| Contaminants | | | | | |
| Total S, ppm | 48 | 29 | 7.8 | 99 | 6.3 |
| Total N, ppm | 751 | 1410 | 318 | 353 | 237 |
| Total Cl, ppm | 113 | 62 | 41 | 70 | 4.7 |
| O in naphtha & distillate, ppm | 250 | — | 574 | — | — |
| Trace Elemental Impurities | | | | | |
| Al, ppm | <1.1 | <0.56 | 0.6 | <0.53 | <0.68 |
| Ca, ppm | 1.4 | 11.5 | <0.5 | <0.53 | <0.68 |
| Fe, ppm | 4.9 | 11.9 | 1.6 | <1.1 | 3.1 |
| Mg, ppm | <0.51 | 1.3 | <0.52 | <0.53 | <0.68 |
| Na, ppm | 2.5 | <0.54 | <1.1 | <2.2 | <2.7 |
| Ni, ppm | <0.51 | <0.54 | <0.52 | 2 | <0.68 |
| V, ppm | <0.51 | <0.54 | <0.52 | 4 | <0.68 |
| P, ppm | 8.2 | 9.9 | <1.6 | <2.2 | 20.2 |
| Si, ppm | 82.5 | 49.6 | 13 | 17 | 3.1 |

ASTM D4052 method was used for specific gravity measurements. Simulated boiling point distribution curve was obtained using ASTM D2887 method. Carlo-Erba analysis for carbon and hydrogen was based on ASTM D5291 method. Bromine number measurement was based on ASTM D1159 method. Hydrocarbon-type analysis was done using a high resolution magnetic mass spectrometer The pyrolysis product is rather pure hydrocarbon made of mostly carbon and hydrogen. The hydrogen to carbon molar ratio varies from 1.7 to near 2.0. The Bromine Number is in the range of 14 through 60 indicating varying degrees of unsaturation coming from olefins and aromatics. The aromatic content is in the range of 5 to 23 volume % with a higher severity unit producing more aromatics. Depending on the process conditions of the pyrolysis unit, the pyrolysis products show paraffinic content ranging from mid-20 vol. % to mid-50 vol. %. The pyrolysis product contains a substantial amount of olefins. Samples A and B, pyrolysis oil produced under more severe conditions such as higher pyrolysis temperature and/or longer residence time, contain higher aromatic and lower paraffinic components, resulting H/C molar ratio of around 1.7 and high Bromine Number of 50-60. Samples C and D were produced at less severe conditions, and the pyrolysis oils are more paraffinic, resulting H/C molar ratio of close to 2.0 and Bromine Number around 40. Sample E, pyrolysis wax, is mostly paraffinic, saturated hydrocarbon with a substantial amount of normal hydrocarbons (as opposed to branched hydrocarbons) with low Bromine Number of only 14.

The following Examples 2 through 5 show the evaluation of waste plastics pyrolysis oil for transportation fuel.

Example 2: Fractionation of Pyrolysis Oil for Evaluation as Transportation Fuel Sample D was distilled to produce hydrocarbon cuts representing gasoline (350° F.⁻), jet (350-572° F.), diesel (572-700° F.) and the heavy (700° F.⁺) fractions. Table 2 summarizes the boiling point distribution and impurity distributions among the distilled product fractions.

TABLE 2

Distillation of Pyrolysis Oil into Fuel Fractions

| Sample ID | Sample D | Sample F | Sample G | Sample H | Sample I |
|---|---|---|---|---|---|
| Intended Fraction | | Gasoline Cut | Jet Cut | Diesel Cut | Unconverted |
| Cut Point Target, ° F. | | 350⁻ | 350-572 | 572-700 | 700⁺ |
| Distillation Actual Yields, wt % | | 37.2 | 38.0 | 15.0 | 9.3 |
| Simulated Distillation, F. | | | | | |
| IBP (0.5 wt %) | 86 | 27 | 299 | 539 | 640 |
| 5 wt % | 154 | 98 | 345 | 557 | 684 |
| 10 wt % | 210 | 147 | 365 | 574 | 696 |
| 30 wt % | 304 | 222 | 416 | 597 | 727 |
| 50 wt % | 421 | 270 | 457 | 619 | 758 |
| 70 wt % | 532 | 291 | 492 | 644 | 808 |
| 90 wt % | 676 | 337 | 546 | 674 | 898 |
| 95 wt % | 743 | 347 | 554 | 683 | 953 |
| FBP (99.5 wt %) | 888 | 385 | 591 | 711 | 1140 |
| Total S, ppm | 99 | 52 | 35 | 80 | 320 |
| Total N, ppm | 353 | 215 | 556 | 232 | 467 |
| Total Cl, ppm | 70 | 181 | 27 | 12 | 13 |

Example 3: Evaluation of Pyrolysis Oil Cut for Gasoline Fuel

Sample F, a pyrolysis oil cut for gasoline fuel boiling range, was evaluated to assess its potential to use as gasoline fuel. Sample F has the carbon number range of C5-C12, typical of the gasoline fuel.

Due to the olefinic nature of the pyrolysis oil, oxidation stability (ASTM D525) and gum forming tendency (ASTM D381) were identified as the most critical properties to examine. Research octane number (RON) and motor octane number (MON) are also the critical properties for engine performance. The RON and MON values were estimated from detailed hydrocarbon GC analysis.

TABLE 3

Evaluation of Pyrolysis Oil Naphtha Fraction for Gasoline Fuel

| | Oxidation Stability, min | Washed Gum, mg/100 mL | RON | MON |
|---|---|---|---|---|
| Sample F | 90 | 5.0 | 71.4 | 67.7 |
| Reference gasoline | >1440 | 1 | 95.8 | 86.2 |
| 4/96 vol. % Blend of Sample F with reference gasoline | >1440 | 2.0 | 94.5 | 85.1 |
| 15/85 vol. % Blend of Sample F with reference gasoline | >1440 | 2.2 | 91.8 | 83.1 |

Sample F, a pyrolysis oil cut for gasoline fuel boiling range, cannot be used by itself as automotive gasoline fuel due to its poor quality. The gasoline fraction from the pyrolysis oil showed very poor oxidation stability in that Sample F failed only after 90 min compared to the target stability of longer than 1440 minutes. The pyrolysis gasoline exceeded the wash gum target of 4 mg/100 mL suggesting severe gum forming tendency. The pyrolysis gasoline has poor octane numbers compared to the reference gasoline. A premium unleaded gasoline was used as the reference gasoline.

We also examined the potential of blending of the pyrolysis gasoline cut for a limited amount to the reference gasoline. Our study showed that possibly up to 15 volume % of Sample F can be blended to the refinery gasoline while still meeting the fuels property targets. By integrating the pyrolysis gasoline product with a refinery fuel, the overall product quality can be maintained.

These results indicate that the as-produced gasoline fraction of pyrolysis oil has limited utility as gasoline fuel. Upgrading in a refinery unit is preferred to convert this gasoline fraction of the pyrolysis oil into hydrocarbon that meets the gasoline fuel property targets.

Example 4: Evaluation of Pyrolysis Oil Cut for Jet Fuel

Sample G, a pyrolysis oil cut for jet fuel boiling range, was evaluated to assess its potential to use as jet fuel. Sample G has the carbon number range of C9-C18, typical of the jet fuel.

Due to the olefinic nature of the pyrolysis oil, jet fuel thermal oxidation test (D3241) was considered as the most critical test. The pyrolysis oil jet cut as-is, Sample G, had only 36 minutes of oxidation stability suggesting the pure pyrolysis jet cut is unsuitable for use as jet fuel.

We prepared a 5 volume % blend of pyrolysis jet cut (Sample G) with refinery produced jet. The blend still failed for the jet fuel oxidation test as shown in Table 4.

TABLE 4

Evaluation of Pyrolysis Oil Jet Fraction for Jet Fuel

| | Jet Fuel Thermal Oxidation Test |
|---|---|
| Reference jet fuel | Passed |
| 5/95 vol. % Blend of Sample G with reference jet fuel | Failed |

These results indicate that the as-produced jet fraction of pyrolysis oil is completely unsuitable for jet fuel, and upgrading in a refinery unit is required to convert this jet fraction of the pyrolysis oil into hydrocarbon that meets the jet fuel property targets.

Example 5: Evaluation of Pyrolysis Oil Cut for Diesel Fuel

Sample H, a pyrolysis oil cut for diesel fuel boiling range, was evaluated to assess its potential to use as diesel fuel. Sample H has the carbon number range of C14-C24, typical of the diesel fuel.

Sample H contains a substantial amount of normal hydrocarbons. Since normal hydrocarbons tends to exhibit waxy characteristics, cold flow properties such as pour point (ASTM D5950-14) and cloud points (ASTM D5773) were considered as the most critical tests.

We prepared two blends at 10 and 20 volume % of Sample H with refinery produced diesel fuel. However, both blends still failed for the target pour point of less than −17.8° C. (0° F.) pour points.

TABLE 5

Evaluation of Pyrolysis Oil Diesel Fraction for Diesel Fuel

|  | Cloud Point (° C.) | Pour Point (° C.) | Pour Point Test |
|---|---|---|---|
| Reference diesel fuel | −17.1 | −19.0 | Passed |
| 10/90 vol. % Blend of Sample H with reference diesel fuel | −11.1 | −12.0 | Failed |
| 20/80 vol. % Blend of Sample H with reference diesel fuel | −5.5 | −7.0 | Failed |

These results indicate that the pyrolysis oil as-is is completely unsuitable for diesel fuel, and upgrading in a refinery unit is required to covert the diesel fraction of pyrolysis oil into hydrocarbon that meets the diesel fuel property targets.

Examples 6: Coprocessing of Pyrolysis Product to FCC Unit or FCC Pretreater Unit Results from Table 1 showed that industrial pyrolysis process of sorted plastics, sourced predominantly from polyethylene and polypropylene waste, produced quality pyrolysis oil or pyrolysis wax made of mostly carbon and hydrogen. With good sorting and efficient pyrolysis unit operation, the nitrogen and sulfur impurities are at low enough levels that a modern refinery can handle cofeeding of pyrolysis feedstocks to their processing units with no detrimental impacts.

However, some pyrolysis oils or wax may still contain high amounts of metals (Ca, Fe, Mg) and other non-metals (S, N, P, Si, Cl, O) that could negatively affect the performance of conversion units in a refinery. For pyrolysis products with high impurity levels are preferentially fed to a FCC feed treater unit before the FCC unit so that bulk of impurities are removed effectively by the pretreater.

By feeding the entire pyrolysis feedstock to a FCC unit as shown in FIG. 2 or to a FCC pretreater unit before the FCC unit, the pyrolysis oil and wax are converted into offgas, LPG paraffins and olefins, FCC gasoline and heavy hydrocarbon components. The FCC gasoline is a valuable gasoline blending component. The heavy fractions, light cycle oil (LCO) and heavy cycle oil (HCO) are converted further in the subsequent conversion units including jet hydrotreating unit, diesel hydrotreating unit, hydrocracking unit and/or coker unit to make more gasoline, jet, and diesel fuel with satisfactory product properties. The LPG paraffins and olefins are either processed further in an alkylation unit or in part used for petrochemicals production with a recycle content. The $C_3$ propane and propylene mix steam is a valuable feedstock for polypropylene generation.

The following Examples 7 and 8 demonstrate the conversion of waste plastics pyrolysis product into quality transportation fuel in a refinery conversion unit, using a FCC unit as an example.

Example 7: Conversion of Pyrolysis Oil in FCC

To study the impact of coprocessing of waste plastics pyrolysis oil to FCC, series of laboratory tests were carried out with Samples A and C. Vacuum gas oil (VGO) is the typical feed for FCC. FCC performances of 20 volume % blend of pyrolysis oil with VGO and pure pyrolysis oil were compared with that of the pure VGO feed.

The FCC experiments were carried out on a Model C ACE (advanced cracking evaluation) unit fabricated by Kayser Technology Inc. using regenerated equilibrium catalyst (Ecat) from a refinery. The reactor was a fixed fluidized reactor using $N_2$ as fluidization gas. Catalytic cracking experiments were carried out at the atmospheric pressure and 900° F. reactor temperature. The cat/oil ratio was varied between 5 to 8 by varying the amount of the catalyst. A gas product was collected and analyzed using a refinery gas analyzer (RGA), equipped with GC with FID detector. In-situ regeneration of a spent catalyst was carried out in the presence of air at 1300° F., and the regeneration flue gas was passed through a LECO unit to determine the coke yield. A liquid product was weighted and analyzed in a GC for simulated distillation (D2887) and $C_5^-$ composition analysis. With a material balance, the yields of coke, dry gas components, LPG components, gasoline (C5-430° F.), light cycle oil (LCO, 430-650° F.) and heavy cycle oil (HCO, 650° F.$^+$) were determined. The results are summarized below in Table 6.

TABLE 6

Evaluation of Pyrolysis Oil Cofeeding to FCC

| Feed | 100% VGO | 20/80 vol % blend, Sample A/VGO | 20/80 vol % blend, Sample C/VGO | 100% Sample A | 100% Sample C |
|---|---|---|---|---|---|
| Cat/Oil, wt/wt | 6.0 | 6.0 | 6.0 | 6.0 | 6.0 |
| Conversion, wt %* | 81.3 | 83.15 | 83.09 | 76.1 | 78.82 |
| WLP Impurity** | | | | | |
| Total O, ppm | 81 | 76 | 62 | 54 | 67 |
| Total N, ppm | 27 | 30 | 33 | 50 | 21 |
| Yields | | | | | |
| Coke, wt % | 4.45 | 4.35 | 4.20 | 3.56 | 2.90 |
| Total Dry Gas, wt % | 2.08 | 1.96 | 1.93 | 1.55 | 1.43 |
| Hydrogen | 0.16 | 0.12 | 0.12 | 0.05 | 0.04 |
| Methane | 0.68 | 0.65 | 0.64 | 0.50 | 0.46 |
| Ethane | 0.44 | 0.43 | 0.41 | 0.33 | 0.28 |
| Ethylene | 0.76 | 0.74 | 0.72 | 0.63 | 0.61 |
| Total LPG, wt % | 21.25 | 21.08 | 21.50 | 20.17 | 24.40 |
| Propane | 1.78 | 1.76 | 1.72 | 1.47 | 1.53 |
| Propylene | 5.53 | 5.51 | 5.56 | 5.57 | 6.75 |
| n-Butane | 1.56 | 1.56 | 1.54 | 1.29 | 1.34 |
| Isobutane | 6.61 | 6.48 | 6.64 | 5.43 | 6.61 |
| C4 olefins | 5.77 | 5.77 | 6.04 | 6.41 | 8.16 |
| Gasoline, wt % | 53.53 | 55.75 | 55.46 | 62.53 | 61.75 |
| LCO, wt % | 12.89 | 12.23 | 11.93 | 10.37 | 8.03 |

TABLE 6-continued

Evaluation of Pyrolysis Oil Cofeeding to FCC

| Feed | 100% VGO | 20/80 vol % blend, Sample A/VGO | 20/80 vol % blend, Sample C/VGO | 100% Sample A | 100% Sample C |
|---|---|---|---|---|---|
| HCO, wt % | 5.81 | 4.63 | 4.98 | 1.82 | 1.50 |
| Octane Number*** | 88.05 | 84.57 | 82.79 | 73.75 | 75.41 |

*Conversion - conversion of 430° F.$^+$ fraction to 430° F.$^-$
**Impurity level of N and O in whole liquid product in fuels boiling range by GC × GC, ppm
***Octane number, (R + M)/2, was estimated from detailed hydrocarbon GC of FCC gasoline.

The results in Table 6 show that up to 20 volume % cofeeding of pyrolysis oil only makes very slight changes in the FCC unit performance indicating coprocessing of pyrolysis oil up to 20% is readily feasible. The 20% blending of Sample A or Sample C led to very slight reduction of coke and dry gas yields, slight increase in gasoline yield and slight decrease in LCO and HCO, which are favorable in most situations. With paraffinic nature of pyrolysis oil, the 20% blends of A and C lowered the Octane number by about 3-5 numbers. With refinery operational flexibility, these octane number debits can be compensated with blending or feeding location adjustments.

The FCC unit cracks the pyrolysis oil info fuel range hydrocarbons, reduces impurities, and isomerize n-paraffins to isoparaffins. All these chemistry will improve the fuel properties of the pyrolysis oil and wax. By cofeeding the pyrolysis oil through the FCC process unit with a zeolite catalyst, the oxygen and nitrogen impurities in the fuel range were reduced substantially, from about 300-1400 ppm N to about 30 ppm N and from about 250-540 ppm O to about 60-80 ppm O. The hydrocarbon composition of all these cofeeding products are well within the typical FCC gasoline range.

The FCC runs of 100% pyrolysis oil showed substantial debits of Octane numbers by about 13-14 numbers. This shows that coprocessing of pyrolysis oil is preferred over processing of pure 100% pyrolysis oil.

Example 8: Coprocessing of Pyrolysis Wax in FCC

To study the impact of coprocessing of waste plastics pyrolysis wax to FCC, series of laboratory tests were carried out with Sample E and VGO. FCC performances of 20% blend of pyrolysis wax with VGO and pure pyrolysis wax were compared with that of the pure VGO feed, similar to Example 7. The results are summarized below in Table 7.

TABLE 7

Evaluation of Pyrolysis Wax Cofeeding to FCC

| Feed | 100% VGO | 20/80 vol % blend, Sample E/VGO | 100% Sample E |
|---|---|---|---|
| Cat/Oil, wt/wt | 6.5 | 6.5 | 6.5 |
| Conversion, wt %* | 82.75 | 84.17 | 91.31 |
| Yields | | | |
| Coke, wt % | 4.78 | 4.76 | 4.26 |
| Total Dry Gas, wt % | 2.11 | 2.05 | 1.79 |
| Hydrogen | 0.16 | 0.14 | 0.07 |
| Methane | 0.69 | 0.67 | 0.58 |
| Ethane | 0.44 | 0.43 | 0.37 |
| Ethylene | 0.78 | 0.77 | 0.73 |
| Total LPG, wt % | 21.71 | 23.15 | 31.79 |
| Propane | 1.87 | 1.93 | 2.28 |

TABLE 7-continued

Evaluation of Pyrolysis Wax Cofeeding to FCC

| Feed | 100% VGO | 20/80 vol % blend, Sample E/VGO | 100% Sample E |
|---|---|---|---|
| Propylene | 5.54 | 5.98 | 8.59 |
| n-Butane | 1.65 | 1.74 | 2.15 |
| Isobutane | 6.91 | 7.25 | 8.88 |
| C4 olefins | 5.74 | 6.25 | 9.89 |
| Gasoline, wt % | 54.16 | 54.21 | 53.47 |
| LCO, wt % | 12.42 | 11.59 | 6.71 |
| HCO, wt % | 4.83 | 4.24 | 1.99 |
| Octane Number** | 89.95 | 88.38 | 83.52 |

*Conversion - conversion of 430° F.$^+$ fraction to 430° F.$^-$
**Octane number, (R + M)/2, was estimated from detailed hydrocarbon GC of FCC gasoline.

The results in Table 7 shows that up to 20 volume % cofeeding of pyrolysis wax only makes very slight changes in the FCC unit performance indicating coprocessing of pyrolysis wax up to 20% is readily feasible. The 20 volume % blending of Sample E led to very slight reduction to no change of coke and dry gas yields, noticeable increase in LPG olefin yield, very slight increase in gasoline yield and slight decrease in LCO and HCO, which are all favorable in most situations. With paraffinic nature of pyrolysis wax, the 20% blend of Sample E lowered the Octane number slightly by 1.5 number. With refinery blending flexibility, this octane number debit can be easily compensated with minor blending adjustments.

The FCC run of 100% pyrolysis wax showed substantial increase in conversion, and debit of the Octane number by 6. This shows that coprocessing of pyrolysis wax is preferred over processing of 100% pyrolysis wax.

Example 9: Feeding of LPG Olefins from FCC Unit, which Coprocessed Waste Plastics Pyrolysis Product, to Refinery Alkylation Unit The pyrolysis oil cofeeding to a refinery FCC unit produces a substantial amount $C_3$-$C_5$ olefins with a recycle content. The $C_4$ only, $C_3$-$C_4$ or $C_3$-$C_5$ stream containing recycled olefins is separated from FCC light-end recovery units, and then fed to an alkylation unit. Reaction of LPG olefins and isobutane in the alkylation reactor produces propane, butane and alkylate gasoline. Alkylate gasoline and butane are very valuable gasoline blending components. The clean propane from the alkylation unit is a valuable feedstock for chemicals manufacturing.

Example 10: Feeding of Recycled $C_3$ for Propylene Production, Followed by Productions of Polypropylene Resin and Polypropylene Consumer Products The clean propane from the alkylation unit, as in Example 9, is dehydrogenated to produce propylene for the polymerization unit for production of polypropylene polymer with a recycle content.

The polypropylene resin containing some recycled-polyethylene/polypropylene derived materials has high quality that is indistinguishable to that of the virgin polypropylene resin made entirely from virgin petroleum resources. The polypropylene resin with the recycled material is then further processed to produce various polypropylene products to fit the needs of consumer products. These polypropylene consumer products now contain chemically recycled, circular polymer while qualities of the polypropylene consumer products are indistinguishable from those made entirely from virgin polypropylene polymer. These chemically recycled polymer products are different from the mechanically recycled polymer products whose qualities are inferior to the polymer products made from virgin polymers.

The foregoing examples together clearly show a new effective way to recycle a large quantity of polyethylene and polypropylene derived waste plastics via chemical recycling through pyrolysis followed by cofeeding of the pyrolysis products in a refinery FCC via efficient integration. This integration allows quality fuels and circular polymer productions.

As used in this disclosure the word "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the composition. The phrase "consisting of" or "consists of" is intended as a transition meaning the exclusion of all but the recited elements with the exception of only minor traces of impurities.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise that as specifically described without actually departing from the spirit and scope of the present invention as defined by the appended claims.

What is claimed is:

1. A continuous process for converting waste plastic into recycle for polypropylene polymerization comprising:
   (a) selecting waste plastics containing polyethylene and/or polypropylene with the waste plastics containing less than 5 wt % of polyethylene terephthalate and polyvinyl chloride;
   (b) passing the waste plastics from (a) through a pyrolysis reactor to thermally crack at least a portion of the polyolefin waste and produce a pyrolyzed effluent;
   (c) separating the pyrolyzed effluent into offgas, a naphtha/diesel fraction, a heavy fraction, and char;
   (d) passing a pyrolysis oil and optionally wax comprising the naphtha/diesel fraction and the heavy fraction to a refinery FCC unit with the volume flow of pyrolysis oil and wax to the FCC unit comprising up to but no more than about 50 volume % of the total hydrocarbon flow to the FCC unit;
   (e) recovering a liquid petroleum gas comprising a $C_3$-$C_5$ olefin/paraffin mixture from the FCC unit;
   (f) passing the liquid petroleum gas fraction to a refinery alkylation unit;
   (g) recovering a propane fraction from the alkylation unit; and
   (h) passing the propane fraction to a dehydrogenation unit to produce propylene.

2. The process of claim 1, wherein the pyrolysis oil and wax of (d) is passed directly to a refinery FCC unit distillation section.

3. The process of claim 1, wherein a gasoline and heavy fraction is recovered from the refinery FCC unit.

4. The process of claim 1, wherein contaminants are removed at the pyrolysis site.

5. The process of claim 1, wherein the propylene produced in (h) is passed on to a propylene polymerization reactor to create polypropylene.

6. The process of claim 5, wherein polypropylene consumer products are prepared from the polymerized polypropylene.

7. The process of claim 1, wherein the waste plastics selected in (a) are from the plastics classification group 2, 4, and/or 5.

8. The process of claim 3, wherein the gasoline recovered from the refinery FCC unit is combined with an alkylate gasoline fraction recovered from the alkylation unit.

9. The process of claim 1, wherein isobutane is added to the liquid petroleum gas stream passed to the refinery alkylation unit.

10. The process of claim 1, wherein gasoline is produced by the FCC and alkylation units and the amount of gasoline produced by the FCC and alkylation units is increased with recycled pyrolysis oil.

11. The process of claim 1, wherein heavy fraction is recovered from the FCC unit distillation column and further processed in the refinery to clean gasoline, diesel, or jet fuel.

12. The process of claim 1, wherein the pyrolysis flow to the FCC unit comprises up to about 20 volume % of the total hydrocarbon flow.

13. A process for converting waste plastic into chemicals useful in preparing polypropylene, comprising:
   (a) selecting waste plastics containing polyethylene and/or polypropylene with the waste plastics containing less than 5 wt % of polyethylene terephthalate and polyvinyl chloride;
   (b) pyrolyzing the waste plastic and recovering a pyrolysis oil and optionally wax comprising a naphtha/diesel fraction and a heavy fraction;
   (c) passing the pyrolysis oil and wax to a refinery FCC unit with the volume flow of pyrolysis oil and wax to the FCC unit comprising up to but no more than about 50 volume % of the total hydrocarbon flow to the FCC unit;
   (d) recovering a $C_3$-$C_5$ olefin/paraffin mixture from the FCC unit;
   (e) passing the $C_3$-$C_5$ mixture to an alkylation unit; and
   (f) recovering propane from the alkylation unit.

* * * * *